United States Patent
Money (10) Patent No.: US 6,289,246 B1
(45) Date of Patent: Sep. 11, 2001

(54) HIGH COMPLIANCE OUTPUT STAGE FOR A TISSUE STIMULATOR

(75) Inventor: David Money, Pennant Hills (AU)

(73) Assignee: Cochlear Pty. Ltd., Lane Cove (AU)

( * ) Notice: Subject to any disclaimer, the term of this patent is extended or adjusted under 35 U.S.C. 154(b) by 0 days.

(21) Appl. No.: 09/244,345

(22) Filed: Feb. 4, 1999

(30) Foreign Application Priority Data

Oct. 13, 1998 (WO) .................................. PCT/AU98/00846

(51) Int. Cl.[7] .............................. A61N 1/36; H04R 25/00
(52) U.S. Cl. ........................ 607/56; 607/12; 607/34; 607/29
(58) Field of Search ......................... 607/11, 12, 28, 607/29, 34, 56, 57

(56) References Cited

U.S. PATENT DOCUMENTS

| | | |
|---|---|---|
| 4,141,064 | 2/1979 | Nagashima . |
| 4,792,886 | 12/1988 | Sahm . |
| 5,372,605 * | 12/1994 | Adams et al. ............................ 607/5 |
| 5,387,228 * | 2/1995 | Shelton .................................. 607/11 |
| 5,391,191 | 2/1995 | Holmstrom . |
| 5,522,865 * | 6/1996 | Schulman et al. ..................... 607/56 |
| 5,869,970 * | 2/1999 | Palm et al. ............................ 324/433 |
| 5,876,423 * | 3/1999 | Braun . |
| 6,035,237 * | 3/2000 | Schulman et al. . |

FOREIGN PATENT DOCUMENTS

WO 96/39005  12/1996  (WO) .

* cited by examiner

*Primary Examiner*—Carl H. Layno
(74) *Attorney, Agent, or Firm*—Gottlieb, Rackman & Reisman, P.C.

(57) ABSTRACT

The output stage of a tissue stimulating apparatus, for example a cochlear implant prosthesis, operating at a low supply voltage (35) incorporates a multiplier circuit (54, 62, 63, 64) for ensuring that voltage compliance is maintained in the event that high intensity stimulations are required. The multiplier circuit makes use of compliance monitoring so that multiplication is only used as required. Also described is a method for operating a tissue stimulating apparatus incorporating a multiplier circuit.

13 Claims, 11 Drawing Sheets

PRIOR ART

HIGH COMPLIANCE OUTPUT STAGE FOR A TISSUE STIMULATOR

BACKGROUND OF THE INVENTION

1. Field of the Invention

This invention pertains to a neural or muscular tissue stimulating prosthesis capable of delivering a high current stimulation signal to a nerve, or brainstem, of a patient and, more particularly, to a cochlear prosthesis with a power supply having an output which can be selectively boosted to a high level.

2. Description of the Prior Art

Though the subject invention will find application with many types of tissue stimulating device it will be described in relation primarily to cochlear prosthesis systems. These prostheses are used to provide therapy to patients suffering from certain hearing impairing conditions. Frequently such systems are of a "two-part" design in that they comprise two sections: an internal or implanted section, and an external section. The external section includes a microphone for receiving ambient sounds and converting them to electrical signals. Power to the external section is provided by a battery. The electrical signals are processed and sent to the implanted section. The implanted section then generates excitation signals to excite the aural nerve of the patient by means of appropriately positioned stimulation electrodes.

Most commonly, the external section of a two-part cochlear prosthesis is inductively coupled by a transcutaneous RF link to the implanted section. The energy of the electrical signals in the RF frequency range is rectified and stored by a power supply located in the internal section. It is that power supply which provides the energy required to power the internal section and to generate the stimulus signals.

More recently there has been a trend in cochlear prosthesis design towards the use of totally implantable prostheses. In such devices the entire cochlear prosthesis, including a battery, is implanted. Obviously it is highly desirable that a totally implanted cochlear prosthesis be of as small a size as possible. In order to achieve the necessary miniaturisation it is important that the power supply, and so by necessity the battery, be of a small size.

To minimise the power requirements of the implanted section of a cochlear prosthesis, whether it be of the totally implanted or of the two-part type, it is desirable to operate it at as low a voltage as possible. One problem however with this approach is that a minimised voltage may present difficulties for the circuitry which is to apply the stimulation currents. In particular, a low operating voltage has hitherto reduced the maximum available amplitude of the stimulating signals that may be generated. An undesirable result is that the dynamic range of the stimulation signals conveyed to the patient is reduced so that loud sounds are perceived by the patient as being quieter than they should be.

Another problem, which is relevant only to cochlear prostheses of the two-part type, is that power supply voltage within the internal section is sensitive to the relative position and spacing of the coils used for the inductive coupling of the internal and external sections. When this positioning is not correct, the intercoil coupling is not optimal, and therefore the available power in the implanted section drops resulting in a limitation of the amplitude of the stimulation current that can be generated into the electrodes.

The problem of insufficient power being available to deliver the appropriate stimulations is especially acute for cochlear prostheses using biphasic stimulation current pulses. These pulses consist of two consecutive phases of opposite polarities with the first phase having a higher peak voltage amplitude than the second phase, due to the capacitive component of the load. If the power supply for the internal section has an inadequate voltage level (i.e., the power supply has a compliance problem), the current during the first phase of a pulse is smaller than required while the current during the second, lower voltage phase, remains unchanged thereby resulting in an unbalanced stimulation pulse.

In order to resolve these problems it has been proposed that, when sufficiently high voltage levels are not available, the duration of the biphasic pulse be increased to compensate, so that the charge delivered during each current phase remains approximately constant. However, the use of longer stimulation pulses inherently reduces the maximum stimulation rate of the device and so is undesirable.

OBJECTIVES AND SUMMARY OF THE INVENTION

In view of the above-named disadvantages of the prior art, it is an objective of the present invention to provide a tissue stimulating system with improved power supply in order to eliminate non-compliant episodes, i.e. episodes in which stimulation pulses are applied which are of less-than-desired current.

A further objective is to provide a tissue stimulating system which selectively increases the voltage available to the stimulation electrodes to a level sufficient to provide suitable cochlear stimulation.

Other objectives and advantages of the invention shall become apparent from the following description.

In particular, a cochlear prosthesis system constructed in accordance with this invention includes a means for receiving and processing ambient sounds to generate processed signals which are applied to the aural nerve through an electrode array. Importantly, the generation of the output signal being delivered to an electrode is monitored and if it is determined to be insufficient a voltage multiplier scheme is used to boost the voltage of the power supply to a high level temporarily, thereby ensuring that the output current can reach the required value.

According to a first aspect of the invention there is provided a tissue stimulating system of the type wherein a power supply and at least one programmable current source are provided for generating a stimulation current of predetermined amplitude, said system further comprising:

a booster circuit for selectively boosting the supply voltage of said power supply when said supply voltage is insufficient to allow said current source to provide a predetermined stimulation current.

According to another aspect of the invention there is provided a cochlear prosthesis system including:

a microphone for picking up ambient sounds;

signal processing circuitry coupled to the microphone for determining stimulation signals corresponding to said ambient sounds;

an electrode array for applying said stimulation signals to the nervous system of a patient;

a power supply for providing energy for the generation of said stimulation signals;

an energy storage device arranged and constructed to selectively supplement said power supply;

a sensor for monitoring the generation of said stimulation signals to determine if said power supply requires supplementation by said energy storage device in order to enable generation of said determined stimulus signals; and a multiplier switching circuit for selectively switching said energy storage device so that it supplements the voltage provided by the power supply in order to ensure that stimulation signals as determined by the signal processor are generated.

Finally, according to yet another aspect of the invention there is provided a method for improving the compliance of the stimulation current output stage of a tissue stimulating system, said output stage including at least one programmable current source and power supply, said method including the steps of:
a) determining if the voltage across each said current source is sufficient to allow generation of a stimulation current of desired amplitude;
b) in the event that said voltage is determined to be insufficient in step a), placing a charged energy storage device in series with said power supply so as to increase the potential voltage across each said programmable current source.

DETAILED DESCRIPTION OF THE INVENTION

Figure 1A:
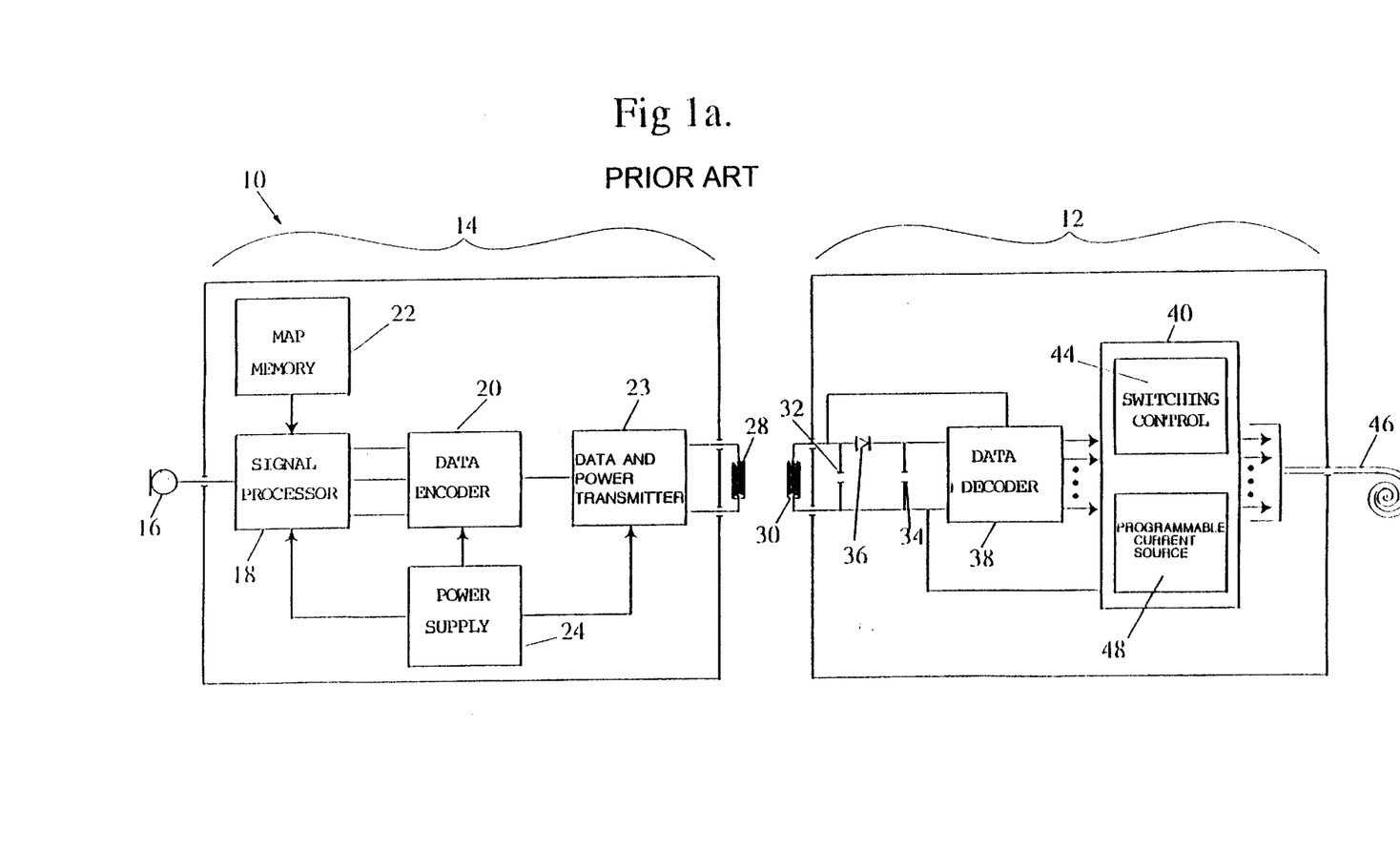
FIG. 1A shows a block diagram of a prior art two-part cochlear prosthesis system.

Referring now to FIG. 1A, an example of a tissue stimulating device being a cochlear prosthesis is depicted. A cochlear prosthesis system 10 of the two-part type consists of an internal or implanted section 12 and an external section 14. The external section 14 includes a microphone 16, a signal processor 18, an encoder 20, and a data and power transmitter 23 as well as a patient map memory 22 and external section power supply 24. Briefly, ambient sounds are picked up by microphone 16 and sent to the signal processor 18. The signal processor detects various components from these sounds and adjusts them according to patient map memory 22 which stores data concerning the patient's perceptual response to stimulation by the cochlear prosthesis. The adjusted data is sent from signal processor 18 to data encoder 20. The encoder converts the data from the signal processor into a serial stream of binary data. A radio frequency signal is amplitude modulated by this data in the power transmitter 23 and transmitted via an RF link to the internal section 12. The RF link consists of two coupled coils 28, 30.

In addition to coil 30, internal section 12 includes a tuning capacitor 32 and rectifier consisting of diode 36 and storage capacitor 34. Coil 30, tuning capacitor 32, diode 36 and storage capacitor 34 comprise the power supply for the internal section. The electrode array control circuitry 40 includes electrode switching control circuits 44 and a programmable current source 48. The data decoder 38 receives the signal transmitted from coil 28 to coil 30 and sends commands to the array control circuitry 40. In response, stimulation signals are applied by the control circuitry 40 to a cochlear electrode array 46. The array 46 is disposed along the patient's basilar membrane (not shown). Except as noted below, the operation of the system 10 is described in U.S. Pat. No. 4,532,930, the contents of which are incorporated herein by reference.

Figure 1B:
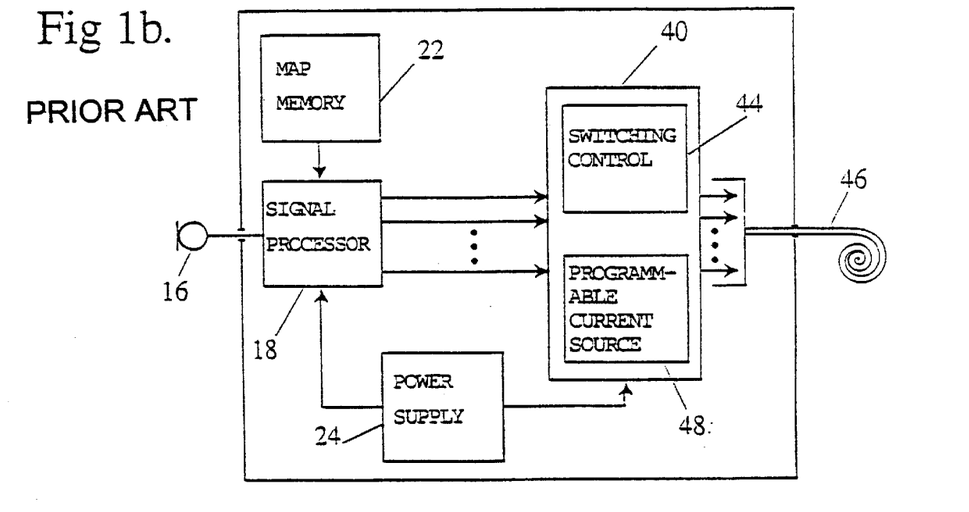
FIG. 1B shows a block diagram of a totally implanted cochlear prosthesis system.

Referring now to FIG. 1B, therein is depicted a block diagram of a totally implantable cochlear prosthesis. The operation of the prosthesis depicted in FIG. 1B is largely analogous to that of the two-part device shown in FIG. 1A, although, because there is no separation of the prosthesis into external and internal sections the decoder, encoder, RF link and rectifier circuitry which appear in two-part designs are not needed. The modules shown in FIG. 1B are highly similar to those of the device depicted in FIG. 1A and therefore the common elements have been identified by the same indicia. The totally implantable prosthesis may be entirely powered by an implanted battery power supply 24.

Figure 2:
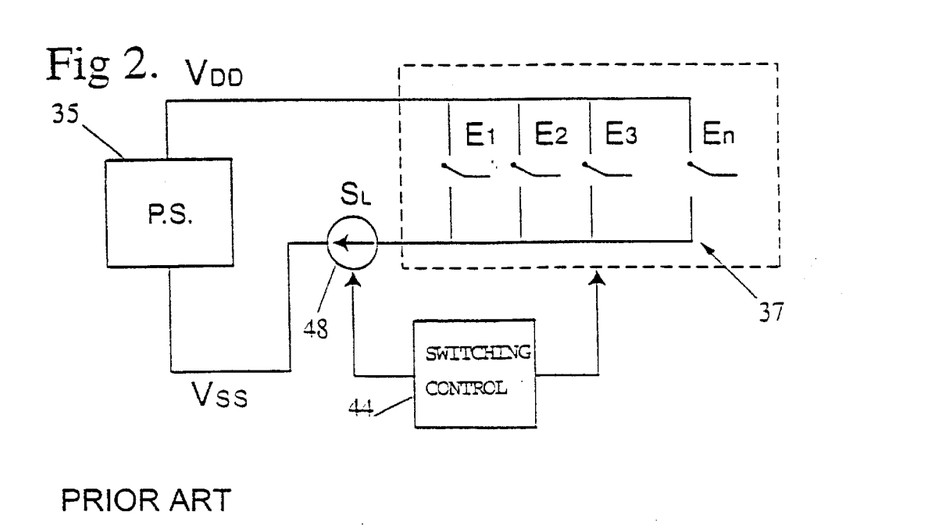
FIG. 2 shows a block diagram of a prior art output stage of a two-part cochlear prosthesis system.

Referring now to FIG. 2, there is depicted a typical prior art output stage as used in two-part cochlear implants for delivering stimulation signals. The arrangement of FIG. 2 includes a plurality of conductors 37-1 to 37-n and electronic switches E1 . . . En controlled by switching control 44. Each of the switches E1 . . . En are used to selectively connect one of the conductors 37-n of array 46 to either Vdd or programmable current source 48. The programmable current source 48 is additionally under command of switching control 44 which sets the amplitude of the stimulations to be generated. Power supply 35 comprises either a tuned circuit, rectifying diode and storage capacitor, as described with reference to FIG. 1 in the case of a two-part prosthesis, or a battery and associated circuitry in the case of a totally implantable cochlear prosthesis.

In order to deliver a stimulation pulse via conductor 37-2, for example, the corresponding switch E2 is set to a first position wherein the conductor 37-2 is connected to the positive rail Vdd. The return path is established through one of the other conductors, such as 37-3 in which case the switch E3 is set so that it is now connected to the programmable current source 48. The current source 48 is set by switching control 44 as discussed above.

Current source 48 is set so that currents of a specified amplitude are passed through the selected electrodes. After a predetermined time the two switches E2, E3 are flipped to the opposite connection thereby reversing their connections to the Vdd rail and current source 48 and in consequence completing the delivery of a biphasic current stimulus pulse through the tissue. It should be noted that although the direction of current through the tissue is reversed, the direction of current out of current source 48 remains constant.

Figure 3:
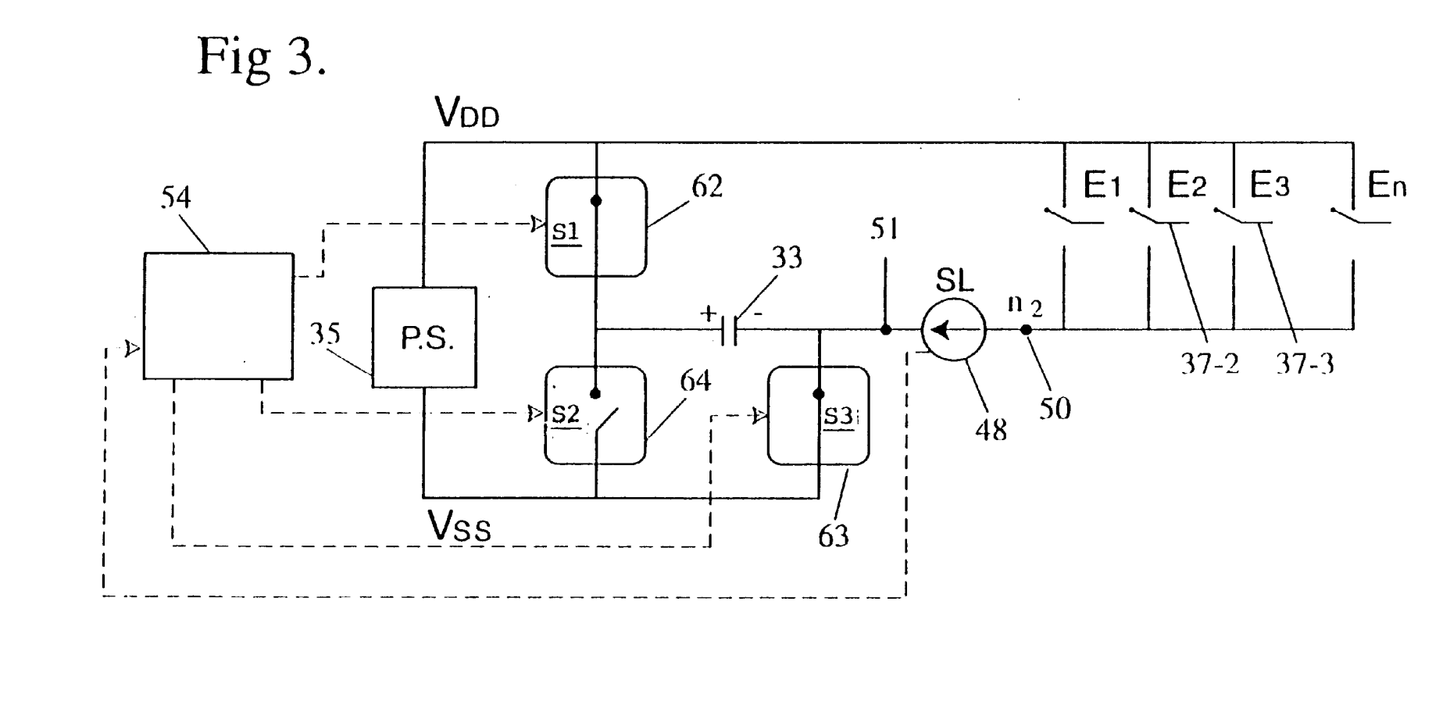
FIG. 3 shows a block diagram of an output stage of a cochlear prosthesis system, either of the two-part or totally implanted type, constructed in accordance with the present invention wherein the standby power supply is in the idle mode.
Figure 4:
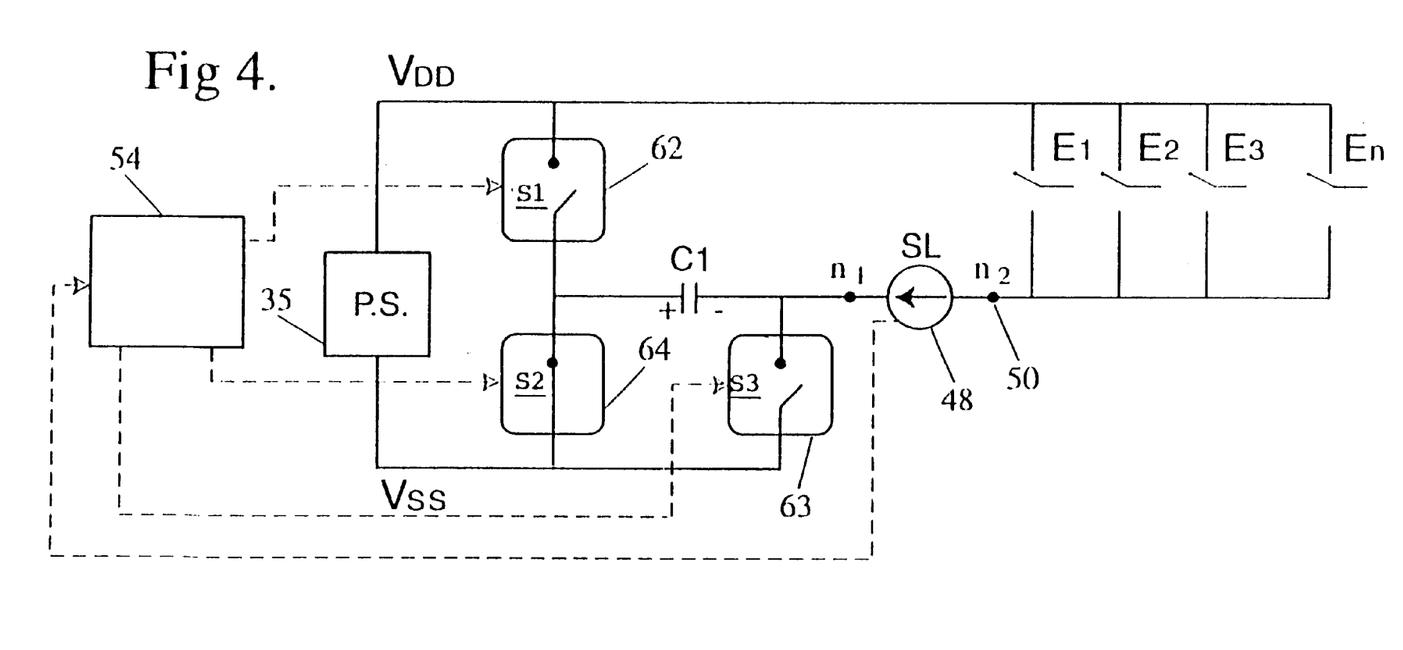
FIG. 4 shows a block diagram of the output stage of a cochlear prosthesis system constructed in accordance with this invention wherein the standby power supply is in the active mode to boost the primary power supply.

As discussed above, one problem with this arrangement is that under certain conditions the voltage across power supply 35 may be insufficient to allow the proper operation of current source 48. With reference to FIG. 2, if the voltage across source 48 falls too low then it will not be possible to attain high current amplitudes. This situation may occur for example when the tissue to be stimulated presents a higher than usual impedance or when it is desired to present an unusually high stimulation. In either case, the potential difference across current source 48 will no longer be sufficient for satisfactory operation of the source. Consequently a non-compliance condition will result. FIGS. 3 and 4 show an improved circuit which remedies this problem.

FIGS. 3 and 4 include components necessary for the implementation of the present invention in a first embodiment, being multiplier switches S1, S2 and S3, labelled 62, 64 and 63, sensing and multiplier switch control circuit 54 and a standby multiplier capacitor C1, 33. It will be noted that by closing multiplier switches 62 and 63 as shown in FIG. 3 the standby multiplier capacitor 33 is placed in parallel with the power supply 35 and in that position will become charged. Furthermore by opening switches S1 and S3 and closing switch S2, as shown in FIG. 4, capacitor 33 is placed in series with the power supply 34 so that the potential difference between node n1, 51 and power rail Vdd is greatly increased. Multiplier control circuit 54 may be implemented using digital logic, alternatively it may be implemented as software running on an implanted microprocessor.

Figure 5:
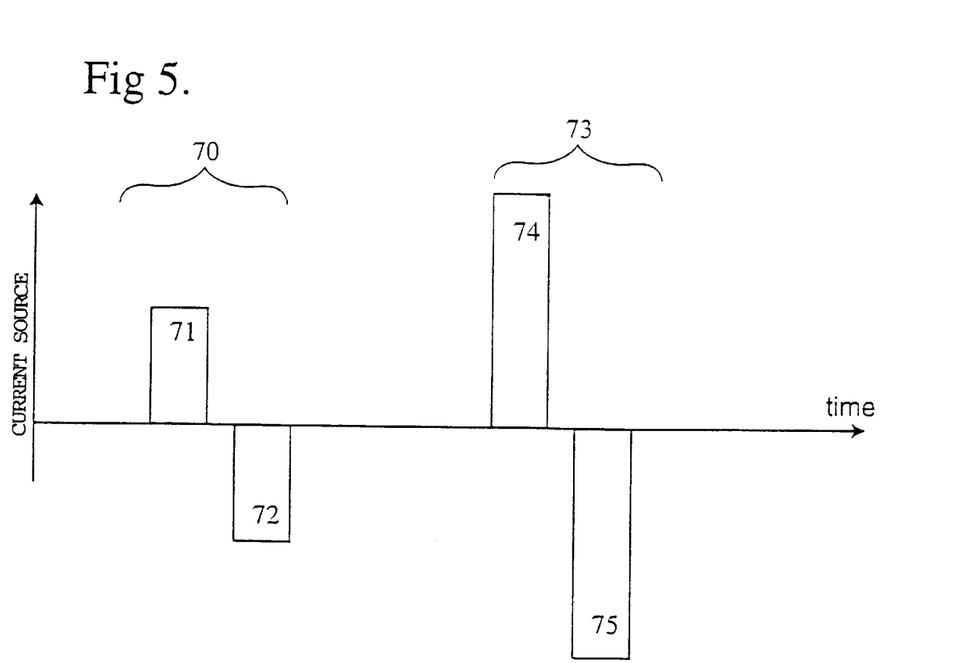
FIG. 5 shows a pair of desired stimulation current waveforms, the second waveform resulting in an otherwise non-compliant condition.

The operation of the circuit of FIGS. 3 and 4 shall now be described in conjunction with the waveshapes of FIGS. 5–8. FIG. 5 depicts the plurality of current waveforms 70 and 73 requested by the switching control 44 to be passed through the load by programmable current source 48. It can be seen that each waveform is biphasic, consisting of two current pulses of equal amplitude and opposite polarity. Thus, lower amplitude biphasic current waveform 70 consists of positive and negative pulses 71 and 72 respectively, and higher amplitude current waveform 73 consists of positive and negative pulses 74 and 75.

Figure 6:
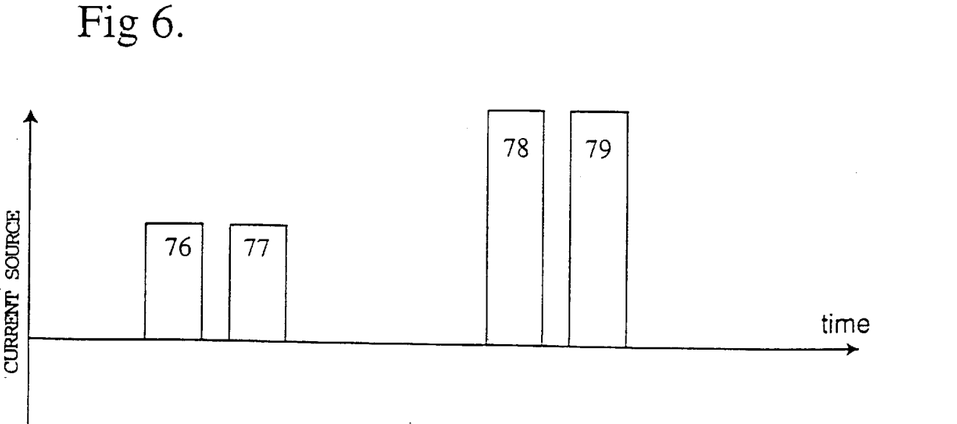
FIG. 6 shows the current that is required to flow in the current source to generate the desired stimulus current of FIG. 5.
Figure 7:
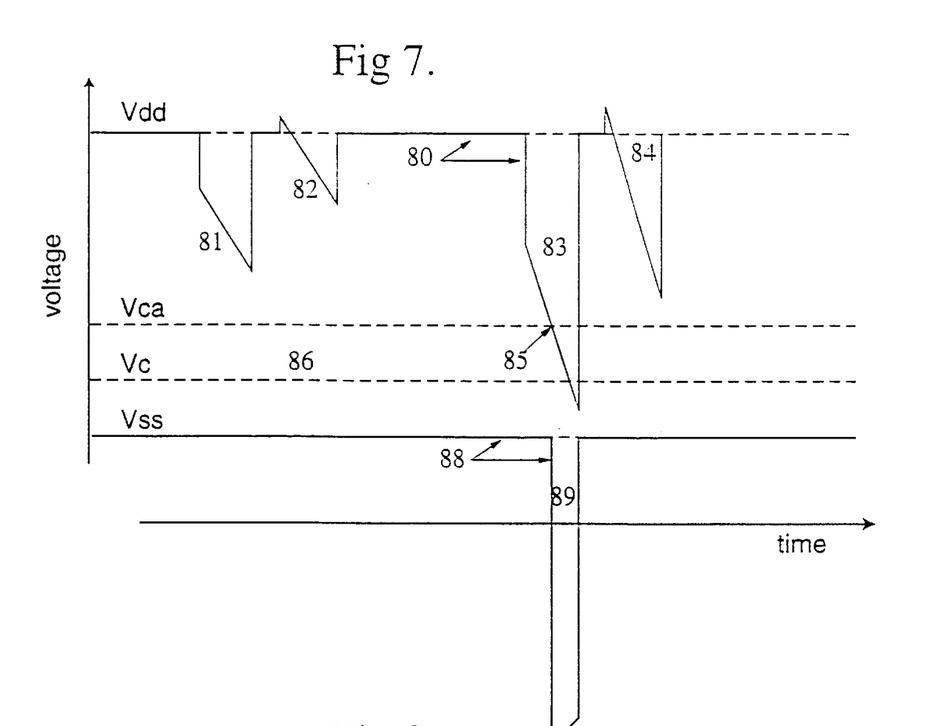
FIG. 7 shows the corresponding voltages at nodes n1 and n2 of FIGS. 3 and 4.

Next, FIG. 6 depicts the corresponding current waveforms that must pass through the controlled current source 48 to produce the desired stimulation current waveforms 70 and 73. The current source must pass two lower amplitude square waves 76 and 77 to generate stimulus pulses 71 and 72 respectively, and two larger amplitude square waves 78 and 79 to generate the stimulus pulses 74 and 75. The current pulse 78 exceeds the capability of the power supply and necessitates a boost, as will be described. In the specific embodiment shown in FIG. 4, this boost is provided by a voltage multiplier as follows:

Referring to FIG. 7 the voltage waveform 80 at node n2 is depicted measured with reference to Vss; and the voltage waveform 88 at node n1 is depicted also measured with respect to Vss. It can be seen from the shape of the voltage waveform 80 that the load contains a capacitive component. The level Vc marks the minimum voltage across the current source 48 (measured as the voltage at n2 with respect to Vss) at which compliance with the desired current waveform of FIG. 6 can be maintained. The voltage Vca is a little higher than Vc and is the trigger control voltage at which a voltage compliance alarm is sensed and voltage multiplier action is commenced. At 85 of the graph in FIG. 7 the voltage 80 at n2 reaches the trigger control voltage Vca. This condition is sensed and, very shortly after, switches 62 and 63 are opened and switch 64 is closed. The reconfiguration of the switches has the effect of placing capacitor C1 between the current source 48 and Vss, consequently pulling the voltage 88 at n1 down to a potential Vdd below Vss. This excursion of the voltage 88 at n1 is shown as the waveform 89 in FIG. 7. After its initial drop at 85 the voltage 88 on n1 subsequently slowly decays towards Vss.

Figure 8:
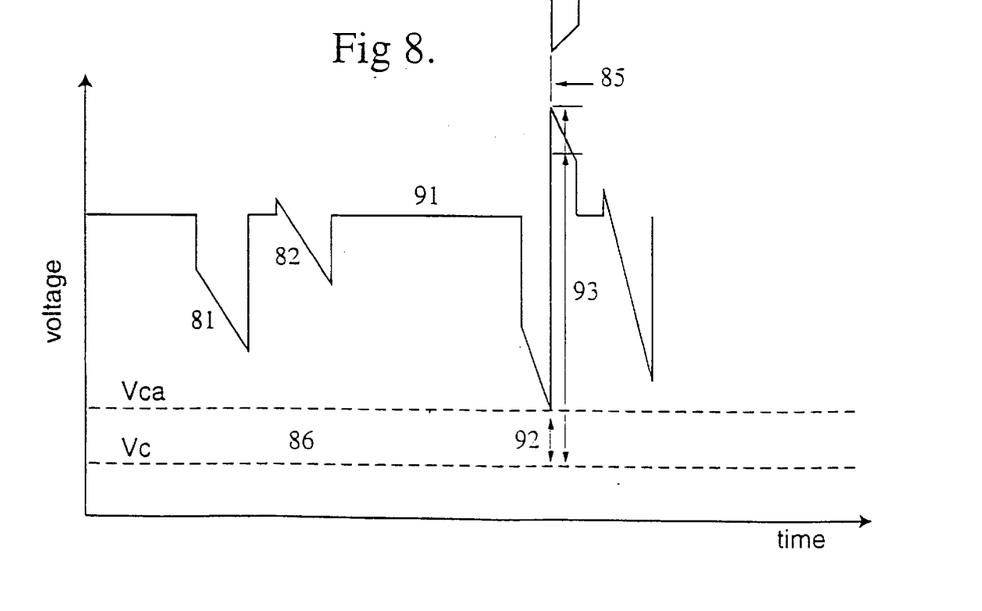
FIG. 8 shows the corresponding voltage waveforms across the current source.

In FIG. 8 the graph depicted shows the voltage waveform levels measured at n2 with respect to n1. With reference to FIG. 8 it is seen that the voltage level across the current source 48 is significantly increased at time 85 and consequently the current compliance margin is increased from the one shown at 92, approaching the voltage compliance limit 86, to the substantial margin 93.

At the completion of the first of the large amplitude pulses 83, switches S1 and S3 are again closed and S2 opened. They remain in that state until another non-compliance state is detected.

Figure 9:
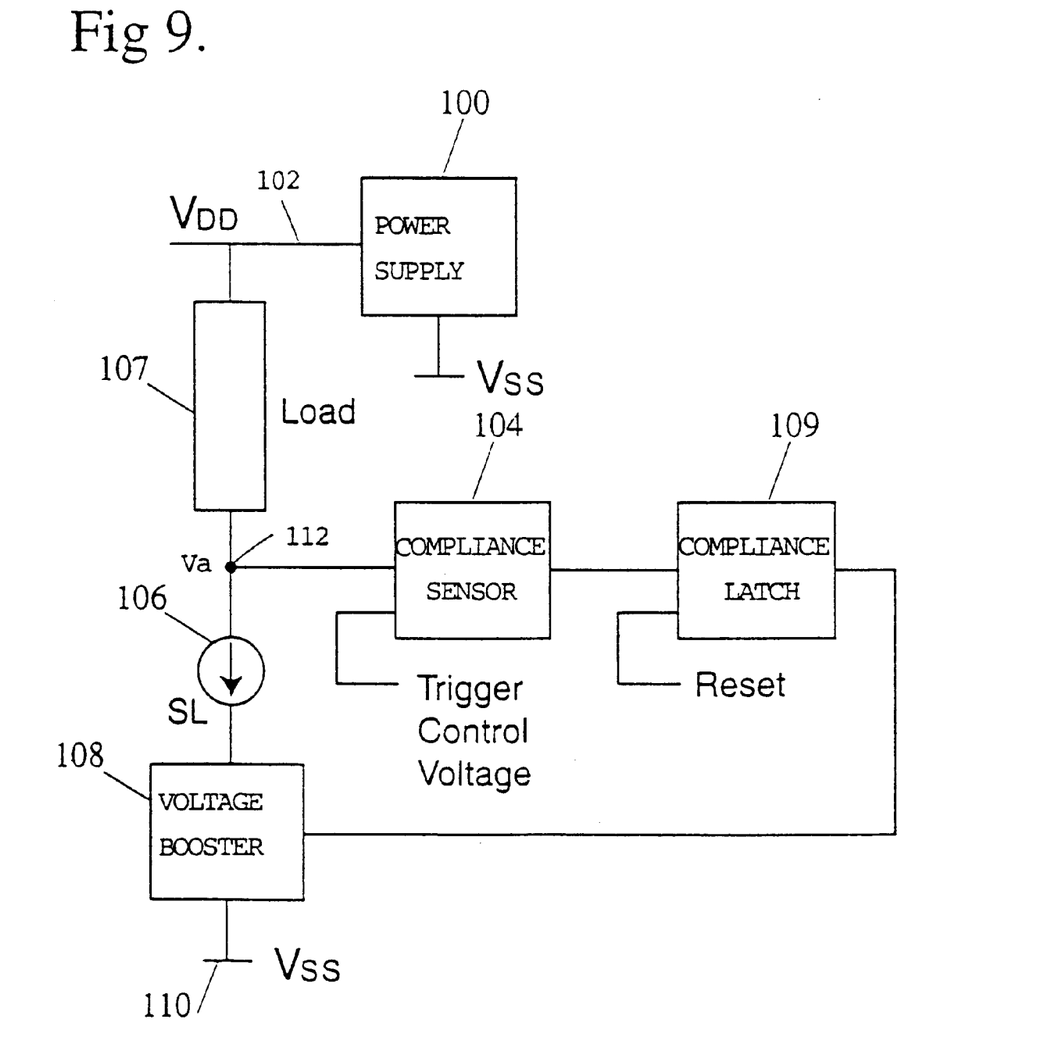
FIG. 9 shows a generalised block diagram of an embodiment of the invention.

FIG. 9 depicts a generalised block diagram of an embodiment of the invention. In this figure a power supply 100 maintains a power rail 102 at a substantially constant voltage Vdd. A settable current source $S_L$ 106 sets the current which flows through the load. In standard operation the current flows through a voltage booster 108 which is internally connected to the low potential rail Vss 110. The voltage Va at point or node 112 is sensed by a compliance sensor 104, which compares the same to a settable trigger control voltage. Should the voltage across the load decrease so that Va falls below the trigger voltage then the compliance sensor will set the compliance latch 109 which will activate the voltage booster 108. The booster pulls down the voltage at point B below Vss so that the potential difference across the current source $S_L$, 106, is increased thereby ensuring the satisfactory operation of the current source and the maintenance of the desired current through the load. It will be realised by those skilled in the art that other arrangements are also possible, for example a re-arrangement of the circuit would make it possible to increase the potential difference across the current source by raising the positive supply with respect to Vdd rather than lowering the negative supply with respect to Vss.

Figure 10:
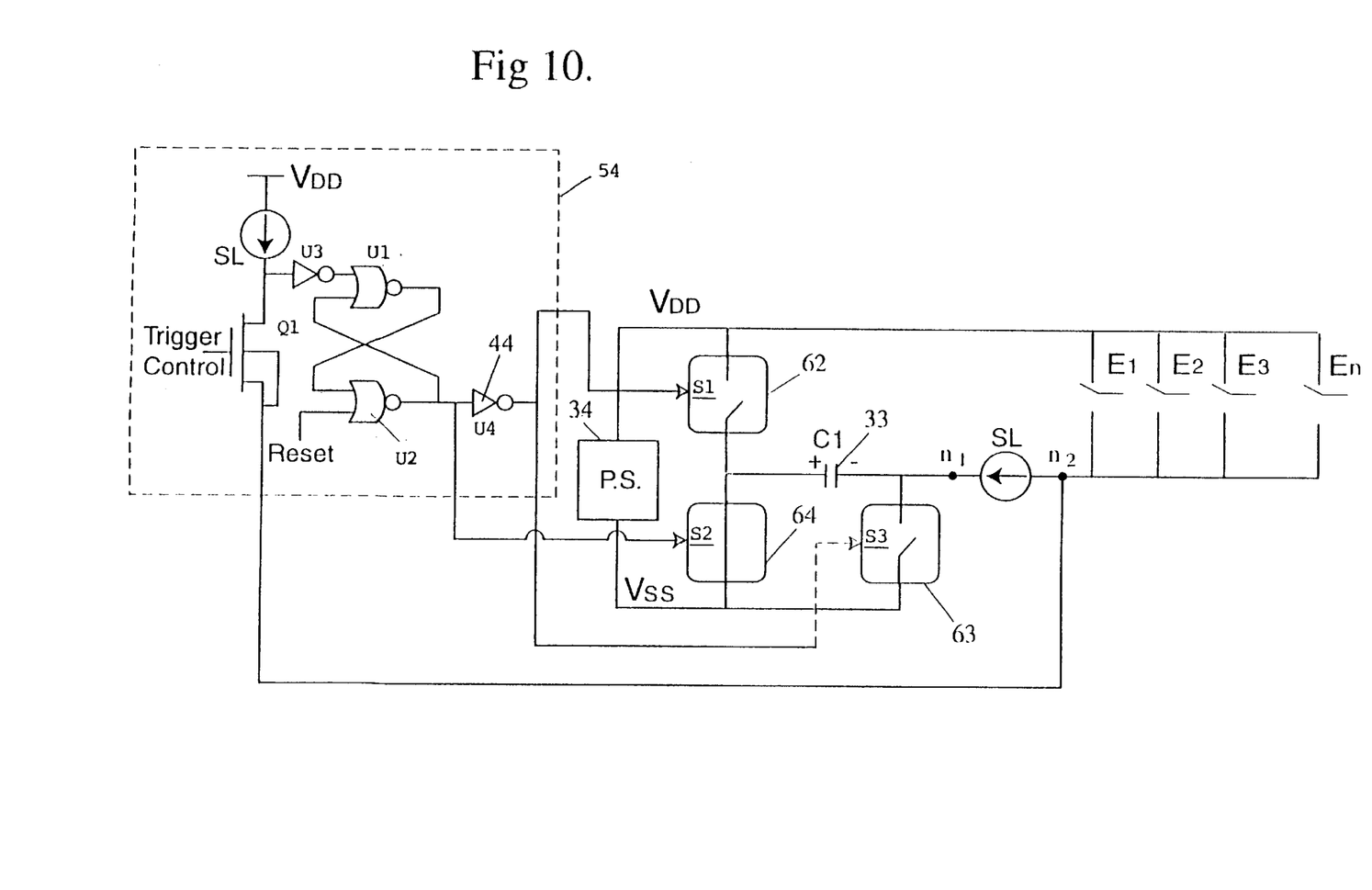
FIG. 10 shows an alternate embodiment of the invention.

FIG. 10 shows an implementation of the arrangement depicted in FIGS. 2 and 4 and therefore the common elements have been identified by the same indicia. In this embodiment, the sensor and control circuit 54 consists of a current source $S_C$, (of much lower amplitude than $S_L$) inverters U3, U4, a FET switch Q1 and two NOR gates U1, U2 connected to form a standard flip-flop latch. The trigger control voltage is provided at the gate of the FET Q1 and its source is used to monitor the voltage at n2, as shown.

Circuit 54 is designed so that when the voltage at n2 falls below a level set by the trigger voltage on the gate of Q1 then the FET Q1 is turned on and the input to U3 falls low. Consequently, the latch formed by U2 and U1 is set and its output goes high. When the output of the latch goes high switch S2 closes and switches S1 and S3 are opened via inverter U4. This operation places C1 in series with the current source $S_L$ which has the effect of pulling the voltage at n1, the negative end of current source $S_L$, down and so prevents $S_L$ from entering a non-compliance state. C1 remains so connected until the end of the stimulation phase at which time the reset input on U2 is set high, switches S1 and S3 close and switch S2 opens. The capacitor C1 is then placed in parallel with the power supply capacitor and recharged. The trigger control voltage (which should be set to the compliance alarm voltage Vca plus the turn on voltage of Q1) can be set by any stable reference voltage e.g., a diode-configured FET or a band-gap reference.

In the illustrated embodiment the power supply voltage in the internal section is boosted simply and efficiently thereby ensuring that sufficient energy is provided to deliver proper stimulation to the electrodes in a short period of time so that adequate charge is delivered without the need to increase the duration of the stimulation pulses. Moreover, this boosting occurs only when it is required. At all other times a lower voltage is provided thereby reducing the overall power consumption of the system. The switches S1–S3 can be manufactured using a modern CMOS IC technology so that the delay in boosting the voltage can be only a few microseconds or less.

Figure 11:
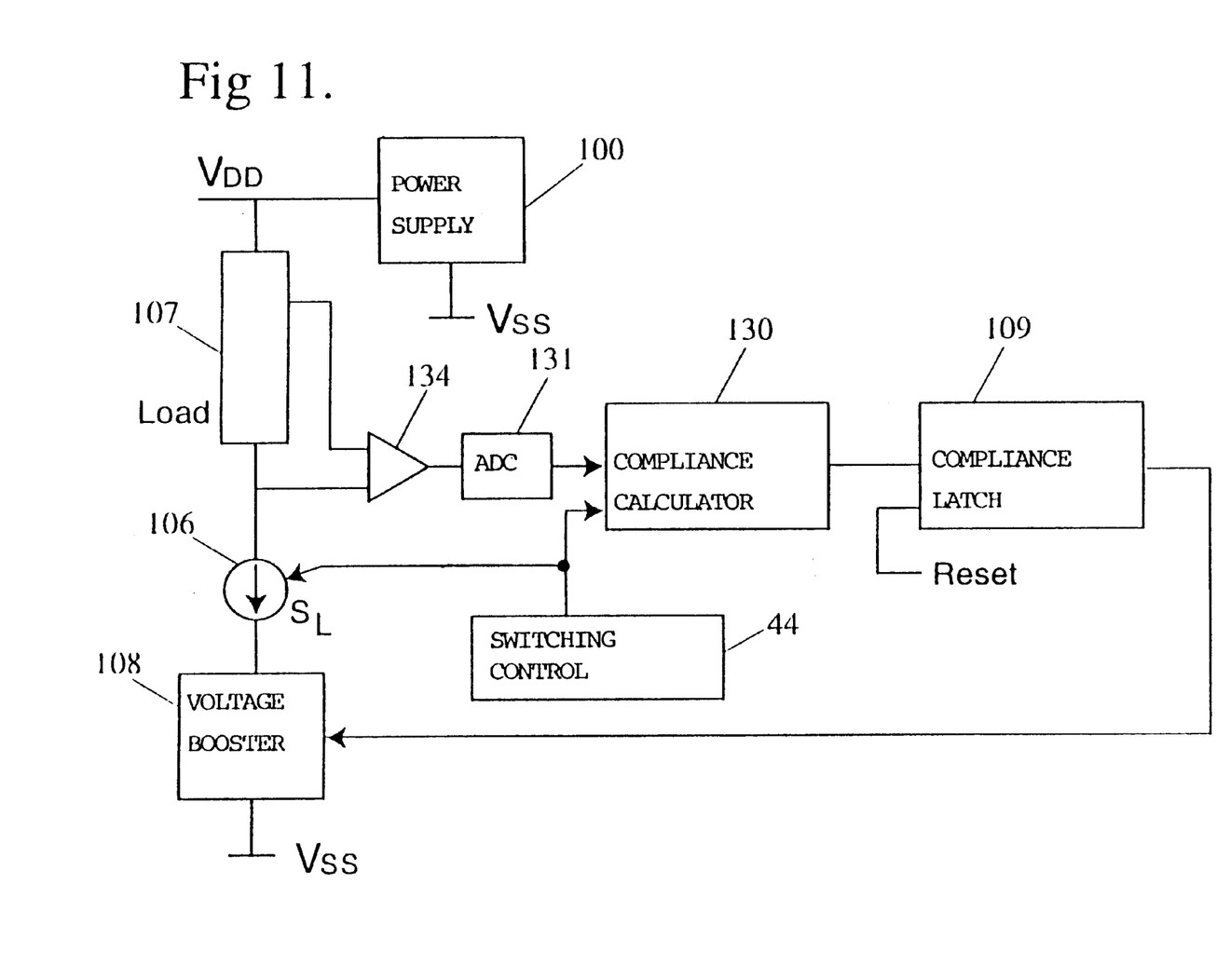
FIG. 11 depicts a further embodiment of the invention.

Referring now to FIG. 11 there is depicted a further embodiment of the invention in which the voltage doubler is activated under command of a compliance calculator. The compliance calculator takes its input from analog to digital converter 131 which is coupled to differential amplifier 134. Differential amplifier 134 determines the voltage Vn drop across the electrode—tissue combination, represented by load 107, of a particular electrode. Given this value of voltage drop, for a current stimulus of particular amplitude, the impedance of the load is readily calculated by compliance calculator 130.

Figure 12:
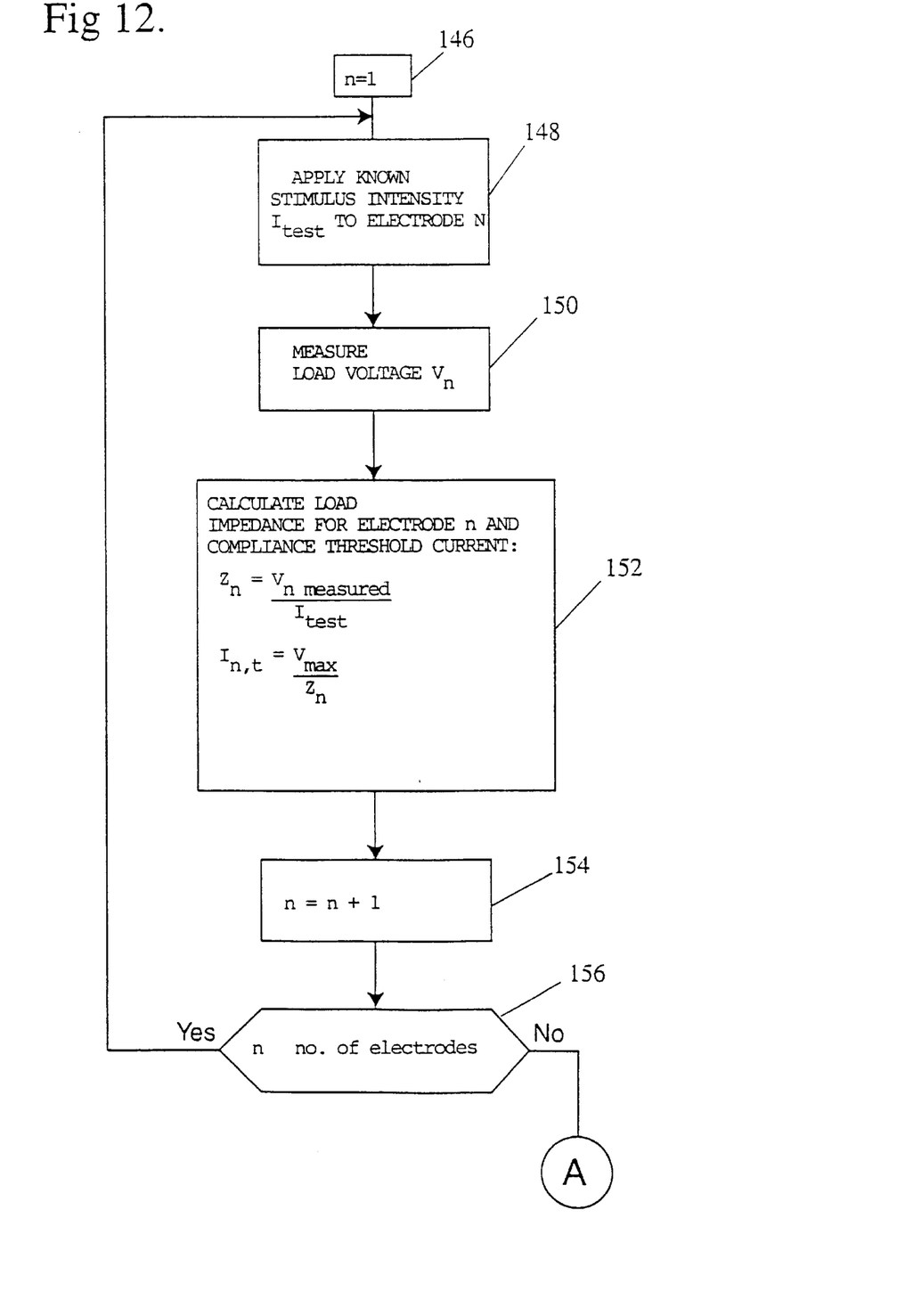
FIG. 12 depicts a flowchart of the operation of the embodiment of FIG. 11 in one mode.

Referring now to FIG. 12 the determination of the threshold current for each electrode by compliance calculator 130 will be explained. This procedure may be performed by the microprocessor that performs the signal processing tasks of the prosthesis or alternatively by a maths co-processor operating under the command of the signal processing microprocessor.

At box 146 the electrode counter variable n is initialised to 1. At box 148 a known current stimulus $I_{test}$ is applied via the nth electrode. At box 150 the voltage Vn across the load 107 is measured by differential amplifier 134 and converted to a digital value, by ADC 131, which is coupled to compliance calculator 130. At box 152 compliance calculator 130 calculates the load impedance for the nth electrode as $Zn=Vn/I_{test}$. The compliance threshold current for the nth electrode, $I_{n,t}$ is then calculated as $I_{n,t}=Vmax/Zn$ where Vmax is the maximum voltage that can be provided across the current source without the aid of voltage boosting. At decision box 156 the electrode counter variable n is tested to see if the calculation procedure has been performed for all of the electrodes. If it has not been so performed then n is incremented at box 154 and the entire procedure repeated for the next electrode until a compliance threshold current has been determined and stored for all of the electrodes.

Figure 13:
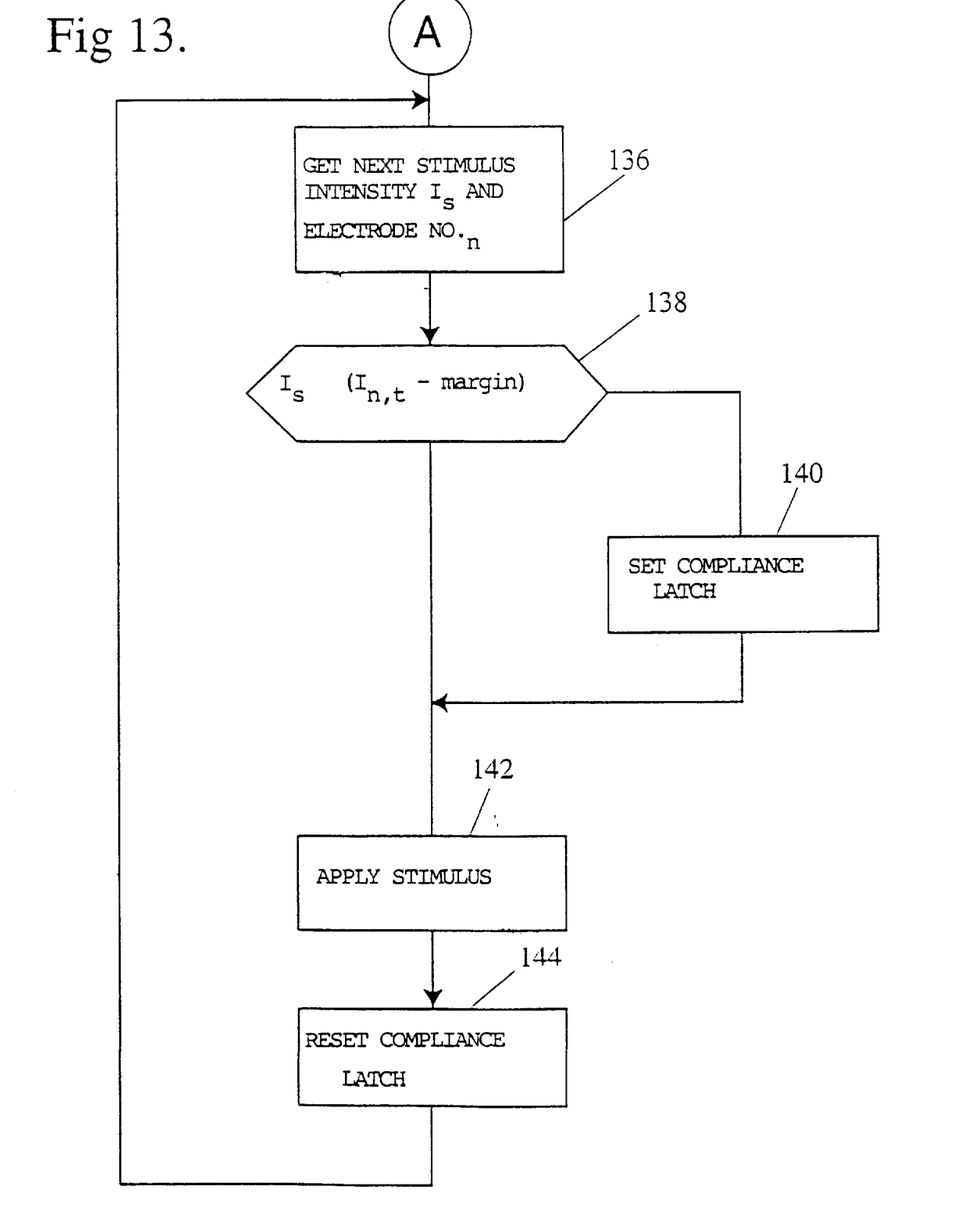
FIG. 13 depicts a flowchart of the operation of the embodiment of FIG. 11 in another mode.

Referring now to FIG. 13 the further operation of the device of FIG. 11 will be explained. At box 136 the controlling microprocessor, for example the same microprocessor that implements signal processor 18 of FIG. 1B, determines the intensity of the next stimulus current $I_s$ and the electrode n via which the stimulus will be delivered.

At decision box 138 the amplitude of $I_s$ is tested to determine if it exceeds the precalculated compliance threshold current for the electrode in question, minus an operational margin. If the result of the test at 138 is positive then the need for voltage boosting is indicated. Control then diverts to box 140 wherein the compliance latch 140 is set so that voltage booster 108 is placed into service. The stimulus is then applied at box 142 and the compliance latch reset subsequent to delivery of stimulus at box 144.

Alternatively, if the result of the test at 138 is negative then no requirement for voltage boosting is indicated and the system proceeds through boxes 142 and 144 without setting the compliance latch.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

What is claimed is:

1. A cochlear prosthesis system comprising:

a power supply;

a programmable current source provided to generate a stimulation current of predetermined amplitude;

a booster circuit for selectively boosting the supply voltage of said power supply when said power supply is insufficient to allow said current source to provide a predetermined current, said booster circuit having a sensor that monitors a parameter indicative of whether said supply voltage is sufficient to provide said stimulation current;

wherein said booster circuit further comprises an energy storage device which is arranged to be charged during periods in which lower or zero stimulation current is flowing and is arranged to supplement the supply voltage during periods in which said supply voltage is insufficient to allow said current of predetermined magnitude to flow.

2. The system of claim 1 further comprising a multiplier switching circuit responsive to said sensing means for selectively switching said energy storage device from a first arrangement, in which it is charged, to a second arrangement, in which it supplements said supply voltage.

3. A cochlear prosthesis system including:

a microphone for picking up ambient sounds;

signal processing circuitry coupled to the microphone for determining stimulation signals corresponding to said ambient sounds;

an electrode array for applying said stimulation signals to the nervous system of a patient;

a power supply for providing energy for the generation of said stimulation signals;

an energy storage device arranged and constructed to selectively supplement said power supply;

a sensing means for monitoring the generation of said stimulation signals to determine if said power supply requires supplementation by said energy storage device in order to enable generation of said determined stimulus signals; and a multiplier switching circuit for selectively switching said energy storage device so that it supplements the power provided by the power supply in order to ensure that stimulation signals as determined by the signal processor are generated.

4. The system of claim 3 wherein said energy storage device is charged during periods between said stimulation pulses.

5. The system of claim 4 wherein said energy storage device is selectively switched from being in parallel with said supply, wherein it is charged, to being in series with said supply wherein it supplements said supply.

6. A method for improving the compliance of the stimulation current output stage of a tissue stimulating system, said output stage including at least one programmable current source and a power source, and at least one stimulation electrode, said method including the steps of:

a) determining if the voltage across each said current source is sufficient to allow generation of a stimulation current of desired amplitudes;

b) in the event that said voltage is determined to be insufficient in step a) for generating one stimulation current having a particular amplitude, connecting a charged energy storage device to said power supply so as to increase the potential voltage across said programmable current source.

7. A method according to claim 6, further including the step of:

for each stimulation electrode, applying a test current in order to measure a load voltage generated across a corresponding tissue-electrode load;

calculating a load impedance on the basis of said load voltage and said test current;

determining the largest unaided stimulation current which can be compliantly delivered by means of said electrode on the basis of the maximum voltage that said power supply is capable of providing unaided.

8. A method according to claim 7, wherein in step b) whether said voltage is determined to be insufficient in step a) comprises:

deciding that said voltage is insufficient if said stimulation current of desired amplitude is substantially greater than said largest unaided stimulation current.

9. A method according to claim 6, wherein said tissue stimulating system comprises a cochlear prosthesis.

10. A method according to claim 8 wherein tissue stimulating system comprises a cochlear prosthesis.

11. A tissue stimulating system comprising:

a power supply having an output;

a programmable current source coupled to said output and adapted to generate current signals of several predetermined magnitudes;

a sensor arranged to monitor power supply and to generate a parameter indicative of whether said power supply is capable of generating said output sufficiently to allow said current source to generate one of said current signals, said current signal having one of said predetermined magnitudes; and a booster responsive to said parameter and adapted to boost said output sufficiently to allow said current supply to generate said one current signal.

12. The tissue stimulating generator of claim 11 wherein said booster is operational only when required to boost the output to generate a current signal of said one predetermined magnitude.

13. A tissue stimulating system comprising:

a power supply having an output;

a programmable current source coupled to said output and adapted to generate current signals of several predetermined magnitudes;

a sensor arranged to monitor power supply and to generate a parameter indicative of whether said power supply is capable of generating said output sufficiently to allow said current source to generate one of said current signals, said current signal having one of said predetermined magnitudes; and a booster responsive to said parameter and adapted to selectively boost said output sufficiently to allow said current supply to generate said one current signal.

* * * * *